United States Patent
Zecchino et al.

(10) Patent No.: US 9,901,532 B2
(45) Date of Patent: *Feb. 27, 2018

(54) ANTI-AGING FORMULATION WITH STABILIZED ASCORBIC ACID AND OTHER ACTIVES

(71) Applicants: Julius Zecchino, New York, NY (US); Alexander Zecchino, Cloister, NJ (US)

(72) Inventors: Julius Zecchino, New York, NY (US); Alexander Zecchino, Cloister, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/330,482

(22) Filed: Sep. 27, 2016

(65) Prior Publication Data

US 2017/0049685 A1    Feb. 23, 2017

Related U.S. Application Data

(63) Continuation-in-part of application No. 14/756,288, filed on Aug. 21, 2015, now Pat. No. 9,717,675.

(51) Int. Cl.

| | |
|---|---|
| *A61K 8/891* | (2006.01) |
| *A61K 31/375* | (2006.01) |
| *A61Q 19/00* | (2006.01) |
| *A61K 31/353* | (2006.01) |
| *A61K 8/67* | (2006.01) |
| *A61K 8/49* | (2006.01) |
| *A61Q 17/04* | (2006.01) |
| *A61K 8/58* | (2006.01) |
| *A61K 8/895* | (2006.01) |
| *A61K 31/05* | (2006.01) |
| *A61K 31/222* | (2006.01) |
| *A61K 31/341* | (2006.01) |
| *A61K 31/60* | (2006.01) |
| *A61K 31/7008* | (2006.01) |
| *A61K 47/24* | (2006.01) |
| *A61K 8/97* | (2017.01) |
| *A61Q 19/08* | (2006.01) |

(52) U.S. Cl.
CPC .............. *A61K 8/891* (2013.01); *A61K 8/498* (2013.01); *A61K 8/585* (2013.01); *A61K 8/676* (2013.01); *A61K 8/895* (2013.01); *A61K 8/97* (2013.01); *A61K 31/05* (2013.01); *A61K 31/222* (2013.01); *A61K 31/341* (2013.01); *A61K 31/353* (2013.01); *A61K 31/375* (2013.01); *A61K 31/60* (2013.01); *A61K 31/7008* (2013.01); *A61K 47/24* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 6,440,433 | B1 * | 8/2002 | Breton | A61K 8/347 424/401 |
| 2002/0018791 | A1 * | 2/2002 | Vatter | A61K 8/891 424/401 |
| 2003/0180395 | A1 * | 9/2003 | Bueter | A61K 36/67 424/725 |
| 2008/0292560 | A1 * | 11/2008 | Tamarkin | A61K 8/046 424/45 |
| 2014/0286882 | A1 * | 9/2014 | Zecchino | A61K 8/891 424/59 |
| 2015/0359893 | A1 * | 12/2015 | Zecchino | A61K 31/353 514/62 |
| 2017/0049686 | A1 * | 2/2017 | Zecchino | A61K 8/891 |

OTHER PUBLICATIONS

Merriam-Webster Online Dictionary, obtained online at: http://www.merriam-webster.com/cgi-bin.dictionary?book-Dictionary&va=derivative, downloaded on Jul. 5, 2008.*

Wermuth, Drug Discovery Today, 2006, 11(7/8), pp. 348-354.*

* cited by examiner

*Primary Examiner* — Abigail Vanhorn

(74) *Attorney, Agent, or Firm* — Dan DeLaRosa

(57) ABSTRACT

The present invention provides for an anti-aging formulation comprising an elastomer, dispersant, active and a drug and related methods of manufacture.

12 Claims, No Drawings

US 9,901,532 B2

ANTI-AGING FORMULATION WITH STABILIZED ASCORBIC ACID AND OTHER ACTIVES

RELATED APPLICATION

This application is a continuation-in-part of U.S. patent Ser. No. 14/756,288 filed on Aug. 21, 2015 entitled "Acne Formulation Having Stabilized Ascorbic Acid and Other Actives", which is a continuation-in-part of U.S. patent Ser. No. 13/999,696 filed on Mar. 18, 2014 entitled "Delivery System Having Stabilized Ascorbic Acid and Other Actives" and issued as U.S. Pat. No. 9,144,564 and issued on Sep. 29, 2015, which is a continuation-in-part of U.S. patent Ser. No. 13/816,000 filed on Mar. 21, 2013 entitled "Delivery System Having Stabilized Ascorbic Acid and Other Actives" and issued as U.S. Pat. No. 9,132,080 and issued on Sep. 15, 2015.

BACKGROUND OF INVENTION

Field of Invention

The present invention relates a delivery system with actives such as ascorbic acid that retain their stability, functionality and aesthetics. In particular, a formulation and related method of manufacture comprising: at least one elastomer; a first dispersant; a second dispersant and at least one active wherein the formulation forms a delivery system wherein the active in the formulation retains its stability, functionality and aesthetics.

Vitamin C, also known as L-ascorbic acid, has been known to be a very important cosmetic active for a long time. It functions as an anti-oxidant, anti-inflammatory, a tyroinase inhibitor (blocking the production of melanin), and a collagen synthesis material. These multi-functional benefits is the reason that vitamin C is so dearly desired to be in cosmetic products. Unfortunately, it is also one of the most unstable materials as well. Vitamin C quickly degrades creating color and odor issues making sale of products containing it not desirable. The industry has created many derivatives to get around this issue. They have not totally been successful either. Limitations on concentration and aesthetics are still a big concern. That being said the most active for is the free L-ascorbic acid, which is stabilized in our composition.

Description of Related Art

The prior art shows that the most crucial problem with any water soluble antioxidant, such as ascorbic acid, is its stability in a formulation. In addition, these antioxidants or actives are crystalline or powder, and would feel like "sand" when formulated into a skin care or cosmetic product. Furthermore, the prior arts' teachings of incorporating these actives into anhydrous systems do not solve the problem. The "feel" of the skin care or cosmetic products using the anhydrous system is undesirable.

The present invention provides for a delivery system wherein the water soluble antioxidant retains its stability, functionality and aesthetics.

SUMMARY OF INVENTION

In one embodiment, the present invention provides for a formulation comprising: at least one elastomer; a first dispersant; a second dispersant and at least one active wherein the formulation forms a delivery system wherein the active in the formulation retains its stability, functionality and aesthetics.

In another embodiment, the elastomer is selected from a group consisting essentially of Dimethicone/Dimethicone crosspolymers, Dimethicone/Vinyldimethicone crosspolymers, Silicone crosspolymers, Silicone, and combination and mixtures thereof. For purposes of this invention, the term "elastomer" is defined as any natural or synthetic material, including polymers, that is able to resume its original shape when a deforming force is removed.

In yet another embodiment, the first dispersant is selected from a group consisting essentially of Cyclomethicone, Isododecane, Hydrocarbons, Esters, Dimethicones, petrolatum, Cyclopentasiloxane, and combination and mixtures thereof.

In still another embodiment, the second dispersant is selected from a group consisting essentially of Dimethicone, Cyclomethicones, Hydrocarbons, Esters, and combination and mixtures thereof. For purposes of this invention, the term "dispersant" is defined as a liquid or gas added to a mixture to promote dispersion or maintain dispersed particles in suspension and also includes any material that is able to gel the elastomer dispersed in it while keeping its structure and stability over time.

In still yet another embodiment, the active is selected from a group consisting essentially of Ascorbic Acid, Epigallo Catechin Gallate (EGCG), Hydroquinone, Ubiquinone, Ubiquinol, Ferrulic Acid, Lipoic acid, and combination and mixtures thereof.

In a further embodiment, the formulation can be used as a product selected from a group consisting of skin care products, cosmetics, cosmeceuticals, pharmaceuticals and nutraceuticals. In another further embodiment, the formulation can be combined with other components and ingredients to form a product selected from a group consisting of skin care products, cosmetics, cosmeceuticals, pharmaceuticals and nutraceuticals.

In yet a further embodiment, the formulation further comprises an activator selected from a group consisting essentially of Water, Glycerin, Glycols, Polyols, Polyglutamic Acid, Hyaluronic Acid, and combination and mixtures thereof.

In still a further embodiment, the formulation further comprises at least one anhydrous system such as bentone cyclomethicone gel with organic sunscreens. For purposes of this invention, the term "anhydrous" is defined as any non-aqueous (no water) or limited water containing formulation or composition.

In still yet a further embodiment, the second dispersant has a viscosity from about 0.65 to about 350 centistoke.

In another embodiment, the present invention provides for a formulation manufactured by a process comprising: admixing at least one elastomer with a first dispersant to form a gel; admixing a second dispersant with the gel; and admixing at least one active with the gel to form a delivery system with an active in the formulation retains its stability, functionality and aesthetics.

In yet another further embodiment, the second dispersant has a viscosity from about 0.65 to about 20 centistoke.

In yet another further embodiment, the process further comprises admixing at least one sunscreen formulation.

In still another further embodiment, the present invention relates to a formulation containing ascorbic acid, and the formulation comprises: at least one elastomer; a first dispersant; a silicone and ascorbic acid wherein the formulation forms a delivery system wherein the ascorbic acid in the formulation retains its stability, functionality and aesthetics.

In still yet another further embodiment, the present invention provides for a formulation manufactured by a process comprising: admixing at least one elastomer with a first dispersant to form a gel; admixing a silicone with the gel; and admixing ascorbic acid with the gel to form a delivery system with an active in the formulation retains its stability, functionality and aesthetics.

In another embodiment, the process further comprises admixing at least one activator selected from a group consisting essentially of Water, Glycerin, Glycols, Polyols, Polyglutamic Acid, Hyaluronic Acid, and combination and mixtures thereof.

In a further embodiment, the present invention relates to a formulation comprising: at least one elastomer less than 50% of the formulation and at least one active from about 0.05 to about 50% of the formulation, and wherein the formulation forms a delivery system wherein said active in said formulation retains its stability, functionality and aesthetics.

In another further embodiment, the present invention relates to a formulation comprising: at least one elastomer less than 50% of the formulation; a first dispersant from about 10 to about 90% of the formulation; a second dispersant from about 2 to about 40% of the formulation and at least one active from about 0.05 to about 50% of the formulation.

In yet another further embodiment, the present invention relates to a formulation comprising: at least one elastomer less than 50% of the formulation; a dispersant from about 10 to about 90% of the formulation; and at least one active from about 0.05 to about 50% of the formulation.

In another embodiment, the present invention relates to a formulation comprising of: at least one elastomer selected from a group consisting of Dimethicone Copolymers in Dimethicone, Vinyldimethicone Copolymers in Dimethicone, Dimethicone crosspolymers in Dimethicone, Vinyldimethicone crosspolymers in Dimethicone, Silicone, and combination and mixtures thereof; at least one dispersant selected from a group consisting of Cyclomethicone, Isododecane, Hydrocarbons, Esters, Dimethicones, petrolatum, Cyclopentasiloxane, and combination and mixtures thereof; at least one active selected from a group consisting of Ascorbic Acid, Epigallo Catechin Gallate (EGCG), Alpha Hydroxy Acids, Hydroquinone, Ubiquinone, Ubiquinol, Ferrulic Acid, Lipoic acid, and combination and mixtures thereof; and at least one drug selected from a group consisting of salicylic acid, benzoyl peroxide, sulfur, resorcinol, and resorcinol monoacetate, and combinations and mixtures thereof.

In yet another embodiment, the formulation further comprises at least one activator selected from a group consisting of Water, Glycerin, Glycols, Polyols, Polyglutamic Acid, Hyaluronic Acid, and combination and mixtures thereof.

In still another embodiment, the formulation further comprises preservatives, said preservatives being selected from a group consisting of phenoxyethanol, sodium benzoate, sorbic acid, alcohol, carpyl glycol, methylparaben, butyl paraben, propylparaben, ethylparaben, heptylparaben, and combination and mixtures thereof.

In still yet another embodiment, the formulation is designed for treatment of acne. In a further embodiment, the drug is an over-the-counter drug.

In yet a further embodiment, the elastomer is from about 5% to about 90% of the formulation; the dispersant is from about 1% to about 40% of the formulation; active is from about 0.1% to about 40% of the formulation; drug is from about 0.5% to about 10% of the formulation; activator is from about 1% to about 50% of said formulation; and the preservative is from about 0.1% to about 5% of the formulation.

In another further embodiment, the present invention provides for a process for manufacturing a formulation, and the process comprises: admixing at least one elastomer with at least one dispersant to form a gel, and the elastomer is selected from a group consisting of Dimethicone Copolymers in Dimethicone, Vinyldimethicone Copolymers in Dimethicone, Dimethicone crosspolymers in Dimethicone, Vinyldimethicone crosspolymers in Dimethicone, Silicone, and combination and mixtures thereof, the first dispersant is selected from a group consisting of Cyclomethicone, Isododecane, Hydrocarbons, Esters, Dimethicones, petrolatum, Cyclopentasiloxane, and combination and mixtures thereof admixing at least one active with the gel to form a delivery system wherein the active in the formulation retains its stability, functionality and aesthetics, the active is selected from a group consisting of Ascorbic Acid, Epigallo Catechin Gallate (EGCG), Alpha Hydroxy Acids, Hydroquinone, Ubiquinone, Ubiquinol, Ferrulic Acid, Lipoic acid, and combination and mixtures thereof; and admixing at least one drug, and the drug selected from a group consisting of salicylic acid, benzoyl peroxide, sulfur, resorcinol, resorcinol monoacetate, and combinations and mixtures thereof to thereby form a formulation with a delivery system.

In another embodiment, the process further comprises admixing at least one activator selected from a group consisting of Water, Glycerin, Glycols, Polyols, Polyglutamic Acid, Hyaluronic Acid, and combination and mixtures thereof.

In yet another embodiment, the process further comprises admixing at least one preservative, and the preservatives are selected from a group consisting of phenoxyethanol, sodium benzoate, sorbic acid, alcohol, carpyl glycol, methylparaben, butyl paraben, propylparaben, ethylparaben, heptylparaben, and combination and mixtures thereof.

In still another embodiment, the present invention relates to an acne treatment formulation comprising of: at least one elastomer selected from a group consisting of Dimethicone Copolymers in Dimethicone, Vinyldimethicone Copolymers in Dimethicone, Dimethicone crosspolymers in Dimethicone, Vinyldimethicone crosspolymers in Dimethicone, Silicone, and combination and mixtures thereof; at least one dispersant selected from a group consisting of Cyclomethicone, Isododecane, Hydrocarbons, Esters, Dimethicones, petrolatum, Cyclopentasiloxane, and combination and mixtures thereof; at least one active selected from a group consisting of Ascorbic Acid, Epigallo Catechin Gallate (EGCG), Alpha Hydroxy Acids, Hydroquinone, Ubiquinone, Ubiquinol, Ferrulic Acid, Lipoic acid, and combination and mixtures thereof; and at least one drug selected from a group consisting of salicylic acid, benzoyl peroxide, sulfur, resorcinol, and resorcinol monoacetate, and combinations and mixtures thereof, wherein said formulation is designed for treatment of acne.

In still another embodiment, the present inventions relates to a formula wherein the collagen building actives are selected from the following group and percent ranges of the entire formulation comprising: peptide from about 0.0001 to about 0.1%, scentella asiatica from about 0.05 to about 2.0%, proteins from about 0.1 to about 10%, TGF from about 0.00001 to about 0.1%, natural extracts from about 0.05 to about 20.00%, glucosamine from about 0.1% to about 40.00%, Resveratrol from about 0.01% to about 2.0%, and combinations and mixtures thereof.

DETAILED DESCRIPTION OF THE INVENTION

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

In one embodiment, the focus of the present invention is stabilizing, inherently, unstable water-soluble anti-oxidants or actives such as Ascorbic Acid (AA), Epigallocatechin Gallate (EGCG), and N-acetyl glucosamine (NAG). These actives help to protect the skin when applied topically, by reducing the action of free radicals that can cause harm to cells. When the molecules are dissolved in water they also are open to oxidation, before they can be applied to skin. When the molecules are in their slid form, they are very stable. One option is to disperse these actives in an essentially anhydrous vehicle, however, the end product is not aesthetically viable for commercial purposes. The actives are crystalline or powder, and would feel like "sand" when formulated into a skin care or cosmetic product and therefore, undesirable to consumers.

In another embodiment, the present invention provides for a solution using gels. The selection of the gelling agent is critical. If the vehicle is too thin, the materials will sink to the bottom and the formula will not be homogeneous, and will not be able to deliver proper doses to the skin. If the vehicle is too thick, it will not apply evenly and the consumer/end user will not like the "feel".

In a further embodiment, using a gel having a cream-like consistency is optimal. It allows the consumer to apply and enjoy the comfort and benefit of the therapy. In another embodiment, the presently claimed invention uses Elastomer technology to achieve the desired results. Dimethicon/vinyldimethicone crosspolymers have been used in cosmetics to create great texture and feel. Interestingly, when one of these molecules is added to the different elastomer gels, the combination is stable but is aesthetically undesirable because you can feel the scratchiness of the dispersed materials. Therefore the right dispersing agents must be used to not only gel the elastomer, but to enable the active materials to blend into the base homogeneously.

The present invention has shown that using Isododecane and Cyclopetasiloxane, and Dimeticone 5cps provides for desired results. Although we recognize that there are other materials that could have a similar effect, to achieve the overall viscosity and texture for a finished formulation that has extraordinary aesthetics a second dispersant is used to fine tune the right consistency. Elastomers are silicone rubbers that have been used in many industries. The finished formula we have is cosmetically commercial and viable. It efficiently stabilizes the actives until they reach the skin. The water proof film that is left on the skin after it is applied, not only is silky smooth and desirable but helps to aid the penetration and keep the active in place, until it can be absorbed.

The following examples are set forth below:

EXAMPLE 1

Vitamin C Formulation

Phase A is weighed in kettle equipped with a high speed agitation. Phase B is then added to Phase A and mixed until homogeneous. Phase C is then slowly admixed with Phase AB and then mixed on very high speed. The ingredients and % of each ingredient in the composition is set forth below in Table 1.

TABLE 1

| Phase: | Ingredients: | INCI | % |
|---|---|---|---|
| A | IDS-5 | Cyclopentasiloxane & Polysilicone-11 & Isododecane | 65.00 |
| B | DC 200 5 cst | Dimethicone | 15.00 |
| C | Vitamin C | Ascorbic Acid | 20.00 |
| | | | 100.00 |

EXAMPLE 2

Vitamin C, N-Acetyl D-Glucosamine & Green Tea Extract Formulation

Phase A is weighed in kettle equipped with a high speed agitation. Phase B is then added to Phase A and mixed until homogeneous. Phase C is then slowly admixed with Phase AB and then mixed on very high speed. The ingredients and % of each ingredient in the composition is set forth below in Table 2.

TABLE 2

| Phase: | Ingredients: | INCI | % |
|---|---|---|---|
| A | IDS-5 | Cyclopentasiloxane & Polysilicone-11 | 59.00 |
| B | DC 200 5 cst | Dimethicone | 15.00 |
| C | Vitamin C | Ascorbic Acid | 20.00 |
| | N-Acetyl D-Glucosamine | N-Acetyl D-Glucosamine | 5.00 |
| | Green Tea Extract | Epigallo Catechin Gallate (EGCG) | 1.00 |
| | | | 100.00 |

EXAMPLE 3

Green Tea Extract Formulation

Phase A is weighed in kettle equipped with a high speed agitation. Phase B is then added to Phase A and mixed until homogeneous. Phase C is then slowly admixed with Phase AB and then mixed on very high speed. The ingredients and % of each ingredient in the composition is set forth below in Table 3.

TABLE 3

| Phase: | Ingredients: | INCI | % |
|---|---|---|---|
| A | IDS-5 | Cyclopentasiloxane & Polysilicone-11 | 93.00 |
| B | DC 200 5 cst | Dimethicone | 5.00 |
| C | Green Tea Extract | Epigallo Catechin Gallate (EGCG) | 2.00 |
| | | | 100.00 |

EXAMPLE 4

N-Acetyl D-Glucosamine Formulation

Phase A is weighed in kettle equipped with a high speed agitation. Phase B is then added to Phase A and mixed until homogeneous. Phase C is then slowly admixed with Phase AB and then mixed on very high speed. The ingredients and % of each ingredient in the composition is set forth below in Table 4.

TABLE 4

| Phase: | Ingredients: | INCI | % |
|---|---|---|---|
| A | IDS-5 | Cyclopentasiloxane & Polysilicone-11 | 82.00 |
| B | DC 200 5 cst | Dimethicone | 10.00 |
| C | N-Acetyl D-Glucosamine | N-Acetyl D-Glucosamine | 8.00 |
| | | | 100.00 |

EXAMPLE 5

Vitamin C Formulation

Phase A is weighed in kettle equipped with a high speed agitation. Phase B is then added to Phase A and mixed until homogeneous. Phase C is then slowly admixed with Phase AB and then mixed on very high speed. Gransil GVL is 85% Coconut Alkanes and 15% Polysilicone-11, there is 24.75% total Silicone in the formulation. The ingredients and % of each ingredient in the composition is set forth below in Table 5.

TABLE 5

| Phase: | Ingredients: | INCI | % |
|---|---|---|---|
| A | Gransil GVL | Coconut Alkanes & Polysilicone-11 | 65.00 |
| B | DC 200 5 cst | Dimethicone | 15.00 |
| C | Vitamin C | Ascorbic Acid | 20.00 |
| | | | 100.00 |

EXAMPLE 6

Vitamin C Formulation

Phase A is weighed in kettle equipped with a high speed agitation. Phase B is then added to Phase A and mixed until homogeneous. Phase C is then slowly admixed with Phase AB and then mixed on very high speed. PC-12 is 85% Isododecane and 15% Polysilicone-11, there is 24.75% total Silicone in the formulation. The ingredients and % of each ingredient in the composition is set forth below in Table 6.

TABLE 6

| Phase: | Ingredients: | INCI | % |
|---|---|---|---|
| A | PC - 12 | Isododecane & Polysilicone-11 | 65.00 |
| B | DC 200 5 cst | Dimethicone | 15.00 |
| C | Vitamin C | Ascorbic Acid | 20.00 |
| | | | 100.00 |

EXAMPLE 7

Vitamin C, N-Acetyl D-Glucosamine & Green Tea Extract Formulation

Phase A is weighed in kettle equipped with a high speed agitation. Phase B is then added to Phase A and mixed until homogeneous. Phase C is then slowly admixed with Phase AB and then mixed on very high speed. Gransil GVL is 85% Coconut Alkanes and 15% Polysilicone-11, there is 23.8% total Silicone in the formulation. The ingredients and % of each ingredient in the composition is set forth below in Table 7.

TABLE 7

| Phase: | Ingredients: | INCI | % |
|---|---|---|---|
| A | Gransil GVL | Coconut Alkanes & Polysilicone-11 | 59.00 |
| B | DC 200 5 cst | Dimethicone | 15.00 |
| C | Vitamin C | Ascorbic Acid | 20.00 |
| | N-Acetyl D-Glucosamine | N-Acetyl D-Glucosamine | 5.00 |
| | Green Tea Extract | Epigallo Catechin Gallate (EGCG) | 1.00 |
| | | | 100.00 |

EXAMPLE 8

Vitamin C, N-Acetyl D-Glucosamine & Green Tea Extract Formulation

Phase A is weighed in kettle equipped with a high speed agitation. Phase B is then added to Phase A and mixed until homogeneous. Phase C is then slowly admixed with Phase AB and then mixed on very high speed. PC-12 is 85% Isododecane and 15% Polysilicone-11, there is 23.8% total Silicone in the formulation. The ingredients and % of each ingredient in the composition is set forth below in Table 8.

TABLE 8

| Phase: | Ingredients: | INCI | % |
|---|---|---|---|
| A | PC-12 | Isododecane & Polysilicone-11 | 59.00 |
| B | DC 200 5 cst | Dimethicone | 15.00 |
| C | Vitamin C | Ascorbic Acid | 20.00 |
| | N-Acetyl D-Glucosamine | N-Acetyl D-Glucosamine | 5.00 |
| | Green Tea Extract | Epigallo Catechin Gallate (EGCG) | 1.00 |
| | | | 100.00 |

EXAMPLE 9

Green Tea Extract Formulation

Phase A is weighed in kettle equipped with a high speed agitation. Phase B is then added to Phase A and mixed until homogeneous. Phase C is then slowly admixed with Phase AB and then mixed on very high speed. Gransil GVL is 85%

Coconut Alkanes and 15% Polysilicone-11, there is 18.95% total Silicone in the formulation. The ingredients and % of each ingredient in the composition is set forth below in Table 9.

TABLE 9

| Phase: | Ingredients: | INCI | % |
|---|---|---|---|
| A | Gransil GVL | Coconut Alkanes & Polysilicone-11 | 93.00 |
| B | DC 200 5 cst | Dimethicone | 5.00 |
| C | Green Tea Extract | Epigallo Catechin Gallate (EGCG) | 2.00 |
| | | | 100.00 |

EXAMPLE 10

Green Tea Extract Formulation

Phase A is weighed in kettle equipped with a high speed agitation. Phase B is then added to Phase A and mixed until homogeneous. Phase C is then slowly admixed with Phase AB and then mixed on very high speed. PC-12 is 85% Isododecane and 15% Polysilicone-11, there is 18.95% total Silicone in the formulation. The ingredients and % of each ingredient in the composition is set forth below in Table 10.

TABLE 10

| Phase: | Ingredients: | INCI | % |
|---|---|---|---|
| A | PC-12 | Isododecane & Polysilicone-11 | 93.00 |
| B | DC 200 5 cst | Dimethicone | 5.00 |
| C | Green Tea Extract | Epigallo Catechin Gallate (EGCG) | 2.00 |
| | | | 100.00 |

Stability tests were also conducted over a six month period and the tests results showed no deterioration of the actives. The stability tests are set for the below in Table 11:

EXAMPLE 11

Acne Formulation 1

Phase A is weighed in kettle equipped with a high speed agitation. Phase B is then added to Phase A and mixed until homogeneous. Phase C is then slowly admixed with Phase AB and then mixed on very high speed. The Gransil GVL is 83.5% Coconut Alkaines and Polysilicone-11, there is 15% Dimethicone, and there is 1.5% total Salicylic Acid in the formulation. The ingredients and % of each ingredient in the composition is set forth below in Table 11.

TABLE 11

| Phase: | Ingredients: | INCI | % |
|---|---|---|---|
| A | Grancil GVL | Isododecane & Polysilicone-11 | 83.50 |
| B | DC 200 5 cst | Dimethicone | 15.00 |
| C | Salicylic Acid | Salicylic Acid | 1.50 |
| | | | 100.00 |

EXAMPLE 12

Acne Formulation 2

Phase A is weighed in kettle equipped with a high speed agitation. Phase B is then added to Phase A and mixed until homogeneous. Phase C is then slowly admixed with Phase AB and then mixed on very high speed. Phase D is then slowly admixed with Phase ABC and mixed on very high speed. The Gransil GVL is 82% Coconut Alkaines and Polysilicone-11, there is 13% Dimethicone, and there is 3% total Sulfur and 2% Resorcinol in the formulation. The ingredients and % of each ingredient in the composition is set forth below in Table 12.

| | | ICC STABILIZED ACTIVE STABILITY DATA | | | | |
|---|---|---|---|---|---|---|
| | Initial | 24 Hour | Month 1 | Month 2 | Month 3 | Month 6 |
| | | | CONTROL VITAMIN C | | | |
| 25° C. | Water White | Water white | Yellow | Dk. Yellow/OJ | Dk. Yellow/OJ | Dk. Yellow/OJ |
| 50° C. | Water White | Sl. Yellow | Dk. Yellow | Deep Orange | Deep Orange | Deep Orange |
| | | | VITAMIN C J116.01 | | | |
| 25° C. | White Cream | White Cream | White Cream | White Cream | White Cream | White Cream |
| 50° C. | White Cream | White Cream | White Cream | White Cream | White Cream | White Cream |
| | | | Vitamin C Anhydrous System J116.02 | | | |
| 25° C. | Sl. Pink Beige | Sl. Pink Beige | Sl. Pink Beige | Sl. Pink Beige | Sl. Pink Beige | Sl. Pink Beige |
| 50° C. | Sl. Pink Beige | Sl. Pink Beige | Sl. Pink Beige | Sl. Pink Beige | Sl. Pink Beige | Sl. Pink Beige |
| | \*Color Only due to natural coloration to EGCG and indicates no degradation or discoloration of formula | | | | | |
| | | | CONTROL EGCG | | | |
| 25° C. | Slight Brown | Slight Brown | Dark Brown | Dark Brown/Red | Dark Brown/Red | Dark Brown/Red |
| 50° C. | Slight Brown | Dk. Brown | Dark Brown/Red | Dark Brown/Red | Dark Brown/Red | Dark Brown/Red |
| | | | EGCG Anhydrous System J116.03 | | | |
| 25° C. | Sl. Pink Beige | Sl. Pink Beige | Sl. Pink Beige | Sl. Pink Beige | Sl. Pink Beige | Sl. Pink Beige |
| 50° C. | Sl. Pink Beige | Sl. Pink Beige | Sl. Pink Beige | Sl. Pink Beige | Sl. Pink Beige | Sl. Pink Beige |
| | \*Color Only due to natural coloration to EGCG and indicates no degradation or discoloration of formula | | | | | |
| | | | N-Acetyl D-Glucosamine Anhydrous System J116.04 | | | |
| 25° C. | White Cream | White Cream | White Cream | White Cream | White Cream | White Cream |
| 50° C. | White Cream | White Cream | White Cream | White Cream | White Cream | White Cream |

TABLE 12

| Phase: | Ingredients: | INCI | % |
|---|---|---|---|
| A | Grancil GVL | Isododecane & Polysilicone-11 | 82.00 |
| B | DC 200 5 cst | Dimethicone | 13.00 |
| C | Sulfer | Sulfer | 3.00 |
| D | Resorcinol | Resorcinol | 2.00 |
| | | | 100.00 |

EXAMPLE 13

Acne Formulation 3

Phase A is weighed in kettle equipped with a high speed agitation. Phase B is then added to Phase A and mixed until homogeneous. Phase C is then slowly admixed with Phase AB and then mixed on very high speed. Phase D is then slowly admixed with Phase ABC and mixed on very high speed. The Gransil GVL is 82% Coconut Alkaines and Polysilicone-11, there is 12% Dimethicone, and there is 3% total Sulfur and 3% Resorcinol Monoacetate in the formulation. The ingredients and % of each ingredient in the composition is set forth below in Table 13.

TABLE 13

| Phase: | Ingredients: | INCI | % |
|---|---|---|---|
| A | Grancil GVL | Isododecane & Polysilicone-11 | 82.00 |
| B | DC 200 5 cst | Dimethicone | 12.00 |
| C | Sulfer | Sulfer | 3.00 |
| D | Resorcinol MonoAcetate | Resorcinol MonoAcetate | 3.00 |
| | | | 100.00 |

EXAMPLE 14

Anti-Aging Pure Vitamin C Formula 1

Phase A is weighed in kettle equipped with a high speed agitation. Phase B is then added to Phase A and mixed until homogeneous. Phase C is then slowly admixed with Phase AB and then mixed on very high speed. Phase D is then slowly admixed with Phase ABC and mixed on very high speed. The ingredients and % of each ingredient in the composition is set forth below in Table 14.

TABLE 14

| Phase: | Ingredients: | INCI | % |
|---|---|---|---|
| A | Gransil GVL | Coconut Alkanes & Polysilicone-11 | 64.9% |
| B | DC 200 5 cst | Dimethicone | 15% |
| C | Vitamin C | Ascorbic Acid | 20% |
| D | Centella Asiatica | Centella Asiatica Extract | .01% |
| | | | 100.00% |

EXAMPLE 15

Anti-Aging Pure Vitamin C Formula 2

Phase A is weighed in kettle equipped with a high speed agitation. Phase B is then added to Phase A and mixed until homogeneous. Phase C is then slowly admixed with Phase AB and then mixed on very high speed. Phase D is then slowly admixed with Phase ABC and mixed on very high speed. The ingredients and % of each ingredient in the composition is set forth below in Table 15.

TABLE 15

| Phase: | Ingredients: | INCI | % |
|---|---|---|---|
| A | Gransil GVL | Coconut Alkanes & Polysilicone-11 | 64.9% |
| B | DC 200 5 cst | Dimethicone | 15% |
| C | Vitamin C | Ascorbic Acid | 20% |
| D | Green Tea Extract | Epigallocatechin gallate | .01% |
| | | | 100.00% |

EXAMPLE 16

Anti-Aging Pure Vitamin C Formula 2

Phase A is weighed in kettle equipped with a high speed agitation. Phase B is then added to Phase A and mixed until homogeneous. Phase C is then slowly admixed with Phase AB and then mixed on very high speed. Phase D is then slowly admixed with Phase ABC and mixed on very high speed. The ingredients and % of each ingredient in the composition is set forth below in Table 16.

TABLE 16

| Phase: | Ingredients: | INCI | % |
|---|---|---|---|
| A | Gransil GVL | Coconut Alkanes & Polysilicone-11 | 64.9% |
| B | DC 200 5 cst | Dimethicone | 15% |
| C | Vitamin C | Ascorbic Acid | 20% |
| D | Green Tea Extract | Epigallocatechin gallate | .01% |
| | | | 100.00% |

EXAMPLE 17

Vitamin C Formulation

Phase A is weighed in kettle equipped with a high speed agitation. Phase B is then added to Phase A and mixed until homogeneous. Phase C is then slowly admixed with Phase AB and then mixed on very high speed. Phase D is then slowly admixed with Phase ABC and mixed on very high speed. The ingredients and % of each ingredient in the composition is set forth below in Table 17.

TABLE 17

| Phase: | Ingredients: | INCI | % |
|---|---|---|---|
| A | Gransil GVL | Coconut Alkanes & Polysilicone-11 | 64.00 |
| B | DC 200 5 cst | Dimethicone | 15.00 |
| C | Vitamin C | Ascorbic Acid | 20.00 |
| D | Green Tea Extract | Epigallocatechin gallate | 1.00 |
| | | | 100.00% |

EXAMPLE 18

Vitamin C Formulation

Phase A is weighed in kettle equipped with a high speed agitation. Phase B is then added to Phase A and mixed until homogeneous. Phase C is then slowly admixed with Phase AB and then mixed on very high speed. The ingredients and % of each ingredient in the composition is set forth below in Table 18.

TABLE 18

| Phase: | Ingredients: | INCI | % |
|---|---|---|---|
| A | PC-12 | Isododecane & Polysilicone-11 | 59.00 |
| B | DC 200 5 cst | Dimethicone | 15.00 |
| C | Vitamin C | Ascorbic Acid | 20.00 |
|   | N-Acetyl D-Glucosamine | N-Acetyl D-Glucosamine | 5.00 |
|   | Green Tea Extract | Epigallocatechin gallate | 1.00 |
|   |   |   | 100.00% |

EXAMPLE 19

Vitamin C Formulation

Phase A is weighed in kettle equipped with a high speed agitation. Phase B is then added to Phase A and mixed until homogeneous. Phase C is then slowly admixed with Phase AB and then mixed on very high speed. The ingredients and % of each ingredient in the composition is set forth below in Table 19.

TABLE 19

| Phase: | Ingredients: | INCI | % |
|---|---|---|---|
| A | Gransil GVL | Coconut Alkanes & Polysilicone-11 | 59.00 |
| B | DC 200 5 cst | Dimethicone | 15.00 |
| C | Vitamin C | Ascorbic Acid | 20.00 |
|   | N-Acetyl D-Glucosamine | N-Acetyl D-Glucosamine | 5.00 |
|   | Green Tea Extract | Epigallocatechin gallate | 1.00 |
|   |   |   | 100.00% |

EXAMPLE 20

Vitamin C Formulation

Phase A is weighed in kettle equipped with a high speed agitation. Phase B is then added to Phase A and mixed until homogeneous. Phase C is then slowly admixed with Phase AB and then mixed on very high speed. The ingredients and % of each ingredient in the composition is set forth below in Table 20.

TABLE 20

| Phase: | Ingredients: | INCI | % |
|---|---|---|---|
| A | Gransil GVL | Coconut Alkanes & Polysilicone-11 | 65.00 |
| B | DC 200 5 cst | Dimethicone | 15.00 |
| C | Vitamin C | Ascorbic Acid | 20.00 |
|   |   |   | 100.00% |

EXAMPLE 21

Vitamin C Formulation

Phase A is weighed in kettle equipped with a high speed agitation. Phase B is then added to Phase A and mixed until homogeneous. Phase C is then slowly admixed with Phase AB and then mixed on very high speed. Phase D is then slowly admixed with Phase ABC and mixed on very high speed. The ingredients and % of each ingredient in the composition is set forth below in Table 21.

TABLE 21

| Phase: | Ingredients: | INCI | % |
|---|---|---|---|
| A | Gransil GVL | Coconut Alkanes & Polysilicone-11 | 64.90 |
| B | DC 200 5 cst | Dimethicone | 15.00 |
| C | Vitamin C | Ascorbic Acid | 20.00 |
| D | Centella Asiatica | Centell Asiatica Extract | 00.10 |
|   |   |   | 100.00% |

The present invention is not limited to the above Examples and Tables. Numerous modifications and variations of the present invention are possible in light of the above teachings. It is therefore to be understood that within the scope of the attendant claims attached hereto, this invention may be practiced other than as specifically disclosed herein.

What is claimed is:

1. A formulation consisting of:
   at least one elastomer selected from a group consisting of Dimethicone Copolymers in Dimethicone, Vinyldimethicone Copolymers in Dimethicone, Dimethicone crosspolymers in Dimethicone, Vinyldimethicone crosspolymers in Dimethicone, Silicone, and combination and mixtures thereof;
   at least one dispersant selected from a group consisting of Cyclomethicone, Isododecane, Hydrocarbons, Esters, Dimethicones, petrolatum, Cyclopentasiloxane, and combination and mixtures thereof;
   at least one active selected from a group consisting of Ascorbic Acid (Vitamin C);
   at least one collagen building active selected from a group consisting of scentella asiatica, peptides, proteins, tissue growth factor (TGF)-Beta, extracts, glucosamine, Resvertrol, Vitamin A, Vitamin B3, Firulic Acid, and combinations and mixtures thereof;
   at least one activator selected from a group consisting of Water, Glycerin, Glycols, Polyols, Polyglutamic Acid, Hyaluronic Acid, and combination and mixtures thereof; and
   at least one preservative being selected from a group consisting of phenoxyethanol, sodium benzoate, sorbic acid, alcohol, carpyl glycol, methylparaben, butyl paraben, propylparaben, ethylparaben, heptylparaben, and combination and mixtures thereof.

2. The formulation of claim 1 wherein said formulation is designed to function as an anti-aging formulation.

3. The formulation of claim 1 wherein said elastomer is from about 5% to about 90% of said formulation.

4. The formulation of claim 1 wherein said dispersant is from about 1% to about 40% of said formulation.

5. The formulation of claim 1 wherein said active is from about 0.1% to about 40% of said formulation.

6. The formulation of claim 1 wherein said activator is from about 1% to about 50% of said formulation.

7. The formulation of claim 1 wherein said preservative is from about 0.1% to about 5% of said formulation.

8. A process for manufacturing a formulation, said process consisting:
    admixing at least one elastomer with at least one dispersant to form a gel, said elastomer is selected from a group consisting of Dimethicone Copolymers in Dimethicone, Vinyldimethicone Copolymers in Dimethicone, Dimethicone crosspolymers in Dimethicone, Vinyldimethicone crosspolymers in Dimethicone, Silicone, and combination and mixtures thereof, said first dispersant is selected from a group consisting of Cyclomethicone, Isododecane, Hydrocarbons, Esters, Dimethicones, petrolatum, Cyclopentasiloxane, and combination and mixtures thereof;
    admixing at least one active with said gel to form a delivery system wherein said active in said formulation retains its stability, functionality and aesthetics, said active is Ascorbic Acid;
    admixing at least one collagen building active selected from a group consisting of scentella asiatica, peptides, proteins, tissue growth factor (TGF)-Beta, extracts, glucosamine, Resvertrol, Vitamin A, Vitamin B3, Firulic Acid, and combinations and mixtures thereof, to thereby form a formulation with a delivery system;
    admixing at least one activator selected from a group consisting of Water, Glycerin, Glycols, Polyols, Polyglutamic Acid, Hyaluronic Acid, and combination and mixtures thereof; and
    admixing at least one preservative, said preservatives being selected from a group consisting of phenoxyethanol, sodium benzoate, sorbic acid, alcohol, carpyl glycol, methylparaben, butyl paraben, propylparaben, ethylparaben, heptylparaben, and combination and mixtures thereof.

9. The process of claim 8 wherein said formulation is designed to function as an anti-aging formulation.

10. An anti-aging formulation consisting of:
    at least one elastomer selected from a group consisting of Dimethicone Copolymers in Dimethicone, Vinyldimethicone Copolymers in Dimethicone, Dimethicone crosspolymers in Dimethicone, Vinyldimethicone crosspolymers in Dimethicone, Silicone, and combination and mixtures thereof;
    at least one dispersant selected from a group consisting of Cyclomethicone, Isododecane, Hydrocarbons, Esters, Dimethicones, petrolatum, Cyclopentasiloxane, and combination and mixtures thereof;
    at least one active is Ascorbic Acid;
    at least one collagen building active selected from a group consisting of scentella asiatica, peptides, proteins, tissue growth factor (TGF)-Beta, extracts, glucosamine, Resvertrol, Vitamin A, Vitamin B3, Firulic Acid, and combinations and mixtures thereof;
    at least one activator selected from a group consisting of Water, Glycerin, Glycols, Polyols, Polyglutamic Acid, Hyaluronic Acid, and combination and mixtures thereof; and
    at least one preservative being selected from a group consisting of phenoxyethanol, sodium benzoate, sorbic acid, alcohol, carpyl glycol, methylparaben, butyl paraben, propylparaben, ethylparaben, heptylparaben, and combination and mixtures thereof, said formulation is designed to treat anti-aging.

11. A method of manufacturing a formulation, said process consisting:
    admixing at least one elastomer with at least one dispersant to form a gel, said elastomer is selected from a group consisting of Dimethicone Copolymers in Dimethicone, Vinyldimethicone Copolymers in Dimethicone, Dimethicone crosspolymers in Dimethicone, Vinyldimethicone crosspolymers in Dimethicone, Silicone, and combination and mixtures thereof, said first dispersant is selected from a group consisting of Cyclomethicone, Isododecane, Hydrocarbons, Esters, Dimethicones, petrolatum, Cyclopentasiloxane, and combination and mixtures thereof;
    admixing at least one active with said gel to form a delivery system wherein said active in said formulation retains its stability, functionality and aesthetics, said active is Ascorbic Acid; and
    admixing at least one collagen building active selected from a group consisting of scentella asiatica, peptides, proteins, tissue growth factor (TGF)-Beta, extracts, glucosamine, Resvertrol, Vitamin A, Vitamin B3, Firulic Acid, and combinations and mixtures thereof to thereby form a formulation with a delivery system.

12. The method of claim 11 wherein said formulation is designed to be an anti-aging formulation.

* * * * *